United States Patent [19]
Koide et al.
[11] Patent Number: 4,992,619
[45] Date of Patent: Feb. 12, 1991

[54] PROCESS FOR SEPARATING METHYL SUBSTITUTED NAPHTHALENE BY CRYSTALLIZATION UNDER PRESSURE

[75] Inventors: Shunichi Koide; Shinji Aihara; Hiroshi Takeshita, all of Tokyo; Harumasa Tanabe; Masami Takao, both of Kobe; Hitoshi Hatakeyama, Kakogawa, all of Japan

[73] Assignees: Showa Shell Sekiyu K.K., Tokyo; Kobe Steel Ltd., Hyogo, both of Japan

[21] Appl. No.: 320,008

[22] Filed: Mar. 7, 1989

[30] Foreign Application Priority Data

Mar. 7, 1988 [JP] Japan ............ 63-51740

[51] Int. Cl.[5] ............ C07C 7/02
[52] U.S. Cl. ............ 585/817
[58] Field of Search ............ 585/812, 813, 816, 817

[56] References Cited

U.S. PATENT DOCUMENTS

| | | | |
|---|---|---|---|
| 2,078,963 | 5/1937 | Miller | 585/817 |
| 2,570,263 | 10/1951 | Nickels et al. | 585/817 X |
| 3,590,091 | 6/1971 | Skarada et al. | 585/813 X |
| 3,855,334 | 12/1974 | Angstadt | 585/817 |

*Primary Examiner*—Glenn Caldarola
*Attorney, Agent, or Firm*—Sughrue, Mion, Zinn, Macpeak & Seas

[57] ABSTRACT

The invention intends to separating a methyl derivative of naphthalene (2,6-dimethyl naphthalene or 2-methyl naphthalene) from a mixture material in a high purity more than 98 weight %. The starting material is preliminarily treated at a raised temperature up to 220° c. at the highest and with LHSV of 0.1-6 $Hr^{-1}$ in the presence of an acid catalyst usually used for olefin polymerization. The treated material is distillated to remove the polymerized impurities and to raise the naphthalene derivative content at least up to 50 weight %. And then the obtained material is subjected to the crystallization under a pressure of 500–2500 $kgf/cm^2$ at a temperature of 80°-150° C. (for 2,6-DMN) or 10°-35° C. (for 2-MN).

17 Claims, 1 Drawing Sheet

PROCESS FOR SEPARATING METHYL SUBSTITUTED NAPHTHALENE BY CRYSTALLIZATION UNDER PRESSURE

BACKGROUND OF THE INVENTION

The invention relates to a process for separating 2,6-dimethylnaphthalene in a high purity of more than 98 weight % from a mixture containing this methyl substituted naphthalene and a process for separating 2-methylnaphthalene in a high purity of more than 98 weight % from a mixture containing this methyl substituted naphthalene. The dimethylnaphthalene and the methylnaphthalene are hereinafter abbreviated respectively, as DMN and MN.

2,6-DMN is oxidized and 2-MN is acylated and then oxidized to produce naphthalene-2,6-dicarboxylic acid, which is an industrially important material for manufacturing polyesters and plasticizers. 2,6-DMN and 2-MN are contained in various fractions of petroleum and coal tar as mixtures together with other DMN and MN isomers.

As for separation of 2,6-DMN and 2-MN from such fractions, various processes have been proposed.

For instance, it is well known to those skilled in the art to cool the DMN fraction obtained by concentrating and extracting petroleum or coal tar material so as to obtain a solid product containing 2,6- and 2,7-DMN, which is then subjected to recrystallization or partial melting in order to separate 2,6-DMN. 2-MN is separated by continuous crystallization or recrystallization of the MN fraction in order to separate 2-MN The DMN compounds, however, generally form eutectic mixtures. For instance, 2,6-DMN and 2,7-DMN form a two-component eutectic mixture in the mole ratio of 41.5:58.5. 2,6- and 2,3-DMN form a two-component eutectic mixture in the mole ratio of 47.5:52.5. Therefore, the conventional process for separating 2,6-DMN of a high purity which relies on the recrystallization method cannot attain a high separation yield, since the yield of 2,6-DMN is based on the material composition.

For instance the fraction of the boiling point of 250°-270° C. obtained by catalytically cracking petroleum contains 8-13% of 2,6-DMN and 8-13% of 2,7-DMN so that when separating and purifying by cooling, solidifying and recrystallizing or partially melting thereof, the yield for recovering of 2,6-DMN is about 30% at the highest.

It is possible to increase the 2,6-DMN content in the material up to 30% by rectification, but it is impossible to considerably change the ratio of 2,6-DMN and 2,7-DMN so the yield of pure 2,6-DMN cannot be raised.

Various fractions from petroleum or coal tar contain 2,6-DMN and 2,7-DMN in the same amount in addition to which various components inclusive of DMN isomers are contained. 2-MN and 1-MN are contained in the fraction in the ratio of 2:1. The boiling points of 2,6-DMN and 2,7-DMN as well as of 2-MN and 1-MN are very close respectively to each other so that the eutectic mixture and the solid solution thereof may be formed.

Thus, separation of 2,6-DMN encounters the problems of decreased recovery yield, difficulty of raising the purity and considerably high cost of separation and purification. The same is applied to separation and purification of 2-MN.

In order to solve the problems referred to above, utilizing crystallization under pressure, has been proposed. This method is superior to recrystallization, partial melting and continuous crystallization based on compactness of the apparatus, lower cost, higher yield and higher purity, but it is disadvantageous in that impurities in the material are subjected to oxidative polymerization with a relatively small amount of oxygen due to local superheat under high pressure in the pressure crystallizing apparatus also, the oxidized polymers become mixed into the separated product crystals.

The crystals of 2,6-DMN and 2-MN separated according to this pressure crystallization method are, thus, colored in black and the qualities thereof are considerably deteriorated due to the oxidized polyme impurities in the material so that the separated products are commercially less valuable. The method also has a disadvantage in that the discharged liquid can not be reused for the reason as referred to above.

SUMMARY OF THE INVENTION

It is an object of the invention, thus, to provide a process for separating methyl substituted naphthalene from the mixture containing thereof without the problems discussed above in the prior art.

It is a particular object to provide processes for separating 2,6-DMN and 2-MN by crystallization under pressure respectively in a high purity of more than 98% by weight without the problems in the prior art discussed above and with a lower cost and a higher yield.

The other objects of the invention and advantageous effects attained thereby will be appreciated by those skilled in the art when studying the full explanation of the invention to be given hereinafter.

Said objects can be attained according to the invention basically by heating a raw material containing 2,6-DMN or 2-MN in the presence of an acid catalyst to polymerize the impurities in the material, and then distilling the treated material to remove the polymerized impurities and to increase the 2,6-DMN or 2-MN content to at least 50 weight %, and subsequently, subjecting the treated material to crystallization at a particular temperature and under a particular pressure.

The reason why the 2,6-DMN or 2-MN content is increased to at least 50 weight %, is that the yield of the object compound is too low, and also the object compound with the high purity more than 98 weight % is not obtained, when the 2,6-DMN or 2-MN content is less than 50 weight %.

Further, by removing the impurities in the starting material, the disadvantages caused by utilizing crystallization under pressure as mentioned above are removed, thereby obtaining the object compound with the high purity.

BRIEF DESCRIPTION OF ACCOMPANYING DRAWINGS

FIG. 1 is a graph showing curves of solid-liquid equilibrium in relation to the temperature and pressure for explaining the crystallization under pressure, and FIG. 2 is a schematic view of the apparatus for carrying out the process according to the invention.

DETAILED DESCRIPTION OF PREFERRED EMBODIMENTS OF THE INVENTION

Figure 1:
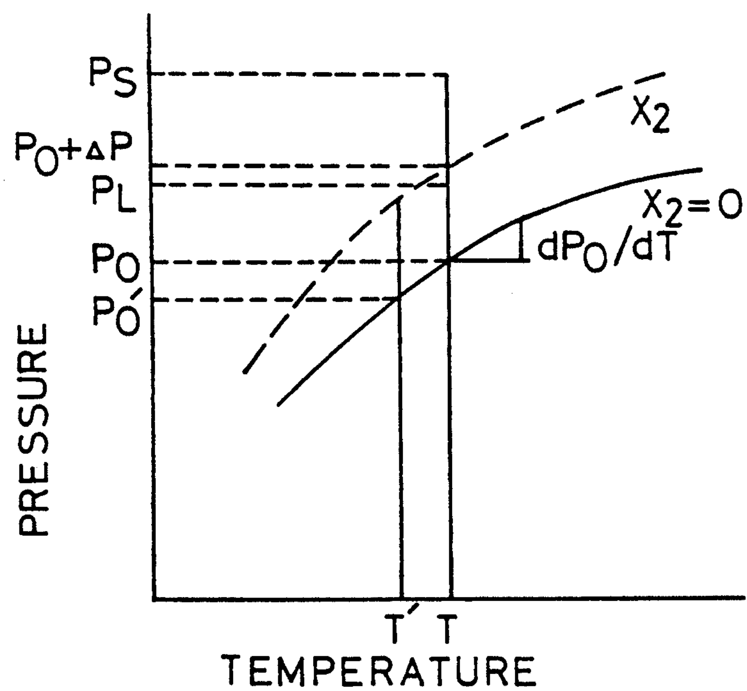

In the invention, a fraction of a boiling point of 250°-270° C., preferably 257°-265° C. (for separation 2,6-DMN) or of 220°-250° C., preferably 235°-245° C.

(for separation of 2-MN) is obtained by catalytically cracking petroleum as the starting material which contains 2,6-DMN or 2-MN and other isomers thereof. This fraction is not subjected directly to crystallization under pressure but rather is heated in the presence of an acid catalyst in advance so as to polymerize impurities such as aromatic hydrocarbons and other unstable substances containing nitrogen, sulphur or oxygen which are apt to be oxidatively polymerized and difficult to be removed e.g. by a simple distillation. The fraction is then distilled so as to increase the 2,6-DMN or 2-MN content to at least 50% by weight, preferably higher than 70% by weight.

The material thus treated in advance is then subjected to crystallization under pressure. Otherwise the yield of the objective compount is low and a high purification more than 98% cannot be expected.

As for raising the 2,6-DMN or 2-MN content in the fraction itself, the cooling crystallization method and the zeolite method are already public knowledge e.g., by U.S. Pat. No. 3,590,091 and JP-B 27,578/1974. According to the former, the cracking fraction containing 2,6-DMN or 2-MN is crystallized at a temperature of −15° to +5° C. (for 2,6-DMN) or −40° to +10° C. (for 2-MN). According to the latter, the DMN fraction is treated at 80°-100° C., with SV 1 g/g/hr in the presence of zeolite Na-Y, and as the occasion demands further subjected to crystallization at a temperature of −35° to +10° C. These treatments, however, are practically not only troublesome but also difficult to sufficiently raise the concentration of 2,6-DMN or 2-MN in the material mixture so that even if the treated material is subjected to crystallization under pressure, the problems referred to above cannot be overcome.

As for the acid catalyst to be used for treating the raw material prior to the pressure crystallization according to the invention, any of the acid catalysts such as sulfuric acid and phosphoric acid can be used e.g., for olefin polymerization. Solid acid catalysts such as silica, alumina, silica-alumina, chromia, titania, zirconia, chromia- alumina, clay, bauxite, zeolite, activated carbon and activated clay also may be used. The surface acidity of the catalyst is of such a degree as to discolor benzeneazodiphenylamine. Suitable properties of the solid catalyst are 100–500 $m^2/g$, preferably 150–300 $m^2/g$ surface area, 30–300 Å, preferably 50–100 Å average pore diameter, 0.1–1.0 cc/g porous volume and 10–100 mesh, preferably 30–60 mesh particle dimension. Particularly desirable acid catalyst for the process of the invention is an activated clay comprising a main content of 2:1 layer structure such as montmorillonite.

The treatment is carried out at a temperature preferably in the range of 120°-200° C. When the temperature is higher than 220° C., disproportionation, isomerization, demethylation and other undesirable side reactions of aromatic compounds contained in the treated mixture material occur. The treatment is done under such a pressure as to keep the material in a liquid phase in relation to the temperature, generally at atomspheric pressure. The liquid phase space velocity (LPSV) of the reaction column is generally 0.1–6 $Hr^{-1}$, and preferably 0.2–2 $Hr^{-1}$.

The starting material to be treated according to the invention prior to crystallization under pressure comprises aromatic compounds and other unstable substances having nitrogen, sulphur or oxygen which are readily oxidized or oxidatively polymerized with a small amount of oxygen at the treatment temperature so as to discolor the product or form undesirable sludge as discussed above.

According to the treatment referred to above, such impurities are polymerized so that they are readily removed from the material by distillation and consequently the DMN or MN content the material is increased up to 70% by weight.

The treated material is then subjected to crystallization under pressure, according to which 2,6-DMN or 2-MN in the liquid mixture material is solidified under a pressure higher than the solid-liquid modification pressure thereof in a sealed vessel so as to exclude the liquid phase from the formed solid-liquid co-existing system and compress the solid phase to "squeeze out" the remaining liquid among solid particles and conglomerate the particles.

Now, expressing a concentration of impurities in the remaining liquid as $X_2$ (molar concentration), a treatment temperature as T (absolute), a solid (crystal)-liquid equilibrium pressure as $P_1$ ($kg/cm^2$), a solid-liquid modification pressure of pure substance as Po ($kg/cm^2$) and a difference between said $P_1$ and Po as $\Delta P$ ($kg/cm^2$), the following relation is established when $X_2$ is of a small value;

$$\Delta P = \frac{RT}{\Delta V} X_2$$

in which R is a gas constant and $\Delta V$ means a volume change per mole caused by solidification (generally a negative value).

Further expressing a statistically average contact pressure at the crystalline interface as $P_S$, a solid-liquid equilibrium pressure of the residual liquid with impurity concentration $X_2$ as $P_O + \Delta P$ and a pressure required to exclude the residual liquid as $P_L$, the relation of $P_O < P_L < P_O + \Delta P < P_S$ is the best for attaining the purpose. As $P_L$ becomes close to $P_O + \Delta P$, the recovered solid amount is decreased and the purifying effect is lowered. When $P_L$ nears to $P_O$, the solid recovering efficiency is slightly lowered but the purification can be efficiently made. It is possible, thus, to obtain the high purity solid in a higher yield only by removing a relatively small amount of the residual liquid, by shifting $P_L$ away from $P_O + \Delta P$ and closer to $P_O$ depending on the concentration and the excluded amount of the residual liquid.

In reference to FIG. 1, a curve gradient of solid-liquid equilibrium $dP_O/dT$ is generally larger than zero. When an absolutely pure substance in which the impurity concentration $X_2 = 0$ is in solid-liquid equilibrium state at a temperature T under a pressure $P_O$, the solid-liquid equilibrium pressure for a substance of impurity concentration $X_2$ is $P_O + \Delta P$. When setting a residual liquid excluding pressure at $P_L$, the solid in the vicinity of the liquid of impurity concentration $X_2$ is melted so that the solid-liquid equilibrium can be made purer. The then statistically average pressure $P_S$ at the crystalline interface is far higher than the pressures referred to above so as to effect a pressure on the crystal particles, whereby the residual liquid is "squeezed out".

When the temperature is lowered down to T' by melting some amount of crystals as a result of setting the excluding pressure at $P_L$, it is possible to adjust the excluding pressure by considering the pressure $P_O'$ as $P_O$ or as a variable to return to the initial value as a result of the temperature recovery.

Figure 2:
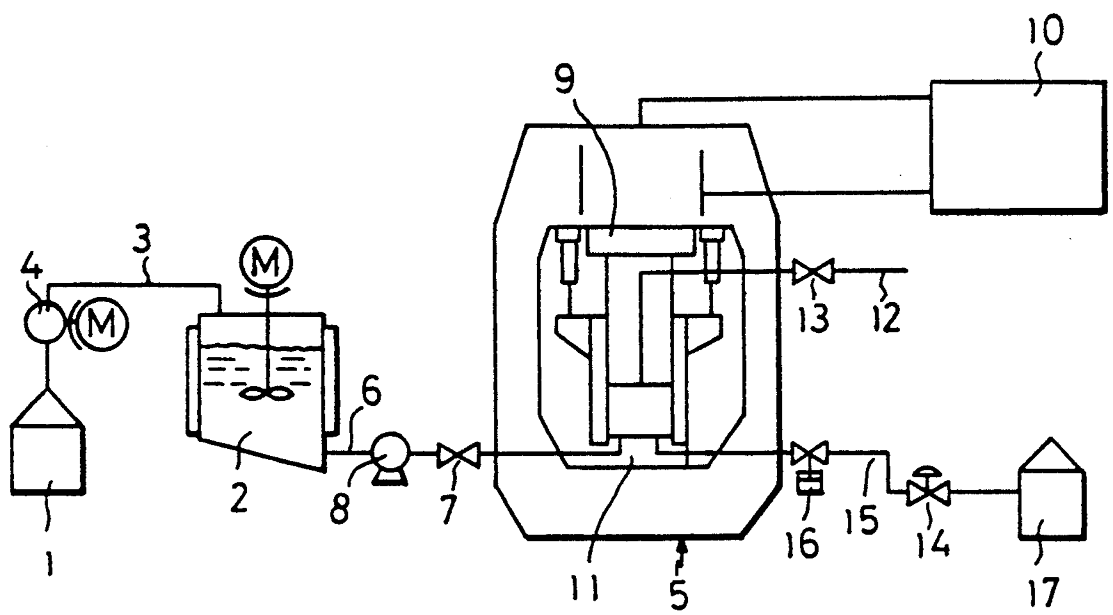

The invention will be more definitely explained in reference to FIG. 2, in which the apparatus for crystallizing under pressure according to the invention is illustrated.

In the case where 2,6-DMN is used for the starting material, the 2,6-DMN contained in 250°–270° C. fraction obtained by catalytically cracking petroleum is preliminarily concentrated (by thermally treating with the acid catalyst and distilling) to obtain a mixture of at least 50 weight %, preferably 70 weight % of 2,6-DMN and another DMN isomer, and then the mixture is preliminarily adjusted to a temperature of 80°–105° C. to form a slurry containing the crystal of 2,6-DMN and the isomer thereof.

In the case where 2-MN is used for the starting material, the 2-MN contained in 220°–250° C. fraction obtained by catalytically cracking petroleum is preliminarily concentrated to obtain a mixture of at least 50 weight %, preferably 70 weight % of 2-MN and another MN isomer and then the mixture is preliminarily adjusted to a temperature of 10°–35° C. to form a slurry containing the crystal of 2-MN and the isomer thereof.

Each mixture is fed from a material tank 1 to a primary crystallization zone 2 through a conduit 3 by means of a motor driven pump 4 to form seed crystals therein. Otherwise, not only is higher pressure needed for primary crystallization but also ultrafine crystals are formed under a supersaturated condition due to the rapid pressurization, which may lead to separation difficulty. Owing to formation of crystaline seeds, the supersaturated condition does not occur, so crystal growth can be started immediately upon pressurization.

The material containing crystalline seeds of 2,6-DMN or 2-MN is then fed to a pressure vessel 5 through a conduit 6 provided with a valve 7 by means of a pump 8.

The pressure vessel 5 comprises a vertically movable piston 9 which is actuated by a hydraulic unit 10 so as to define a chamber 11 for crystallization under pressure between the free end of the piston 9 and the bottom wall of the chamber 11 in which pressure may be raised by lowering the piston down.

The piston is preferably arranged with a conduit for overflow provided with a valve 13 and opened at the piston free end so that when the supplied material is filled in the chamber 11 to flow into the conduit 12, the overflow is detected to close the valves 7, 13 and the piston 9 is lowered to raise the pressure in the chamber.

Thereby, the material in the chamber 11 is made in the solid-liquid coexisting state as discussed above. The resulting 2,6-DMN or 2-MN in solid state is already of a high purity. As the solidification thereof progresses, the temperature increases, but it is generally preferable not to cool the system.

The temperature after the pressure is raised adiabatically up to 500–2500 kgf/cm$^2$, at which the solid-liquid separation is started, affects the purity and yield of the product. Thus, the temperature of the material to be supplied is controlled at 80°–105° C. in case of 1,2-DMN and at 10°–35° C. in case of 2-MN as discussed above taking into consideration, in advance, specific heat, solidification latent heat and so on of the mixture material so that a desired temperature can be held.

Then, a valve 14 is opened for discharging the liquid content in the crystallizing chamber 11 through a conduit 15 via a decompressor 16 into a waste liquid tank 17, while maintaining the pressure in the chamber 11 by lowering the piston 9 down. The crystal particles of 2,6-DMN or 2-MN are thus pressed so as to "squeeze out" the remaining liquid contents, which are exhausted out of the chamber 11 into the tank 17.

As the piston 9 is further lowered, the crystal particles are further pressed to form a large mass in the form of the decreased volume of chamber 11. When the liquid content in the solid phase is almost completely excluded and discharged out of the chamber, the liquid phase pressure is correspondingly decreased so that crystalline surfaces are partially melted to increase the degree of purification by virtue of the so-called "sweating effect". Thereby the purity of the separated 2,6-DMN or 2-MN product reaches 98% or more.

Then, the piston is raised up to the initial position and the product is taken out by opening the lid provided in the bottom wall of the pressure vessel 5.

The invention will be explained in more detail in reference to following Examples.

EXAMPLE 1

The starting material comprising 67 weight % of 2,6-DMN, other DMN isomers inclusive of 9 weight % of 2,7-DMN and a small amount of impurities were preliminarily treated in the presence of activated clay as an acid catalyst. The properties thereof were as follows:

| | |
|---|---|
| (1) Particle dimension | 30–60 mesh |
| (2) Bulk density | 0.63 |
| (3) Specific surface area | 281 m$^2$/g |
| (4) Porous volume | 0.39 ml/g |
| (5) Average pore diameter | 55 Å |
| (6) Free acid | 2.6 mg KOH/g |
| (7) Chemical composition | (wt %) |
| $SiO_2$ | 76.0 |
| $Al_2O_3$ | 10.3 |
| $Fe_2O_3$ | 1.7 |
| CaO | <0.1 |
| MgO | 1.5 |
| Ignition loss | 10.0 |

The starting material was passed through the activated clay at a temperature of 160° C. with 0.5 Hr$^{-1}$ of LPSV and then subjected to distillation to remove polymerized impurities so as to obtain a colorless oily material.

This mixture material was continuously heated at 200° C. for 200 hours in air in a sealed glass tube with almost no change from the initial state.

The mixture material was subjected to preliminary crystallization to form crystalline seeds of 2,6-DMN. The material in the slurry state was fed to a pressure vessel of the hydraulic piston-cylinder structure and subjected to an adiabatic pressure of 1500 kgf/cm$^2$. Then, the liquid phase in the pressure vessel was discharged therefrom while maintaining the pressure, and 2,6-DMN crystals were pressed until the liquid phase pressure fell down to 200 kgf/cm$^2$.

Obtained crystalline 2,6-DMN was not colored and had a purity of about 98%.

EXAMPLE 2

The starting material comprising 65 weight % of 2-MN, 7 weight % of 1-MN and a small amount of impurities were preliminarily treated similar to Example 1.

The obtained oily colorless material was continuously heated similar thereto with no substantial change.

The material was subjected to crystallization under pressure as in Example 1 except the temperature of the supplied material was controlled to 5° C.

Obtained crystalline 2-MN was not colored and had a purity of about 98%.

The residual mother liquors in Examples 1 and 2 were cyclically used in the subsequently repeated treatment.

What is claimed is:

1. A process for separating a methyl substituted naphthalene comprising the steps of preliminarily treating a starting mixture material containing said methyl substituted naphthalene in the presence of an acid catalyst at a raised temperature to polymerized impurities in the material, removing said polymerized impurities from the starting mixture, and crystallizing said material under pressure whereby the methyl substituted naphthalene content is increased so as to obtain the methyl substituted naphthalene in a high purity more than 98% by weight.

2. The process as set forth in claim 1, in which the preliminarily treated mixture material, which is to be subjected to the crystallization under pressure, has a 2,6-dimethyl naphthalene content increased to at least 50% by weight.

3. The process as set forth in claim 1, in which the preliminarily treated mixture material, which is to be subjected to the crystallization under pressure, has a 2-methyl naphthalene content increased to at least 50% by weight.

4. The process as set forth in claim 2, in which the preliminarily treated mixture material containing 2,6-dimethyl naphthalene, of which temperature is controlled to be 80°-105° C., is subjected to the crystallization under a pressure of 500-2500 kgf/cm$^2$.

5. The process as forth in claim 3, in which the preliminarily treated mixture material containing 2-methyl naphthalene, of which temperature is controlled to be 10°-35° C., is subjected to the crystallization under a pressure of 500-2500 kgf/cm$^2$.

6. The process as set forth in claim 1, in which the starting mixture material is preliminarily treated in the presence of the acid catalyst at a raised temperature up to 220° C. at the highest and with a liquid phase space velocity of 0.1-6 Hr$^{-1}$.

7. The process as set forth in claim 6, in which the starting mixture material containing dimethyl naphthalenes is a fraction with b.p. of 250°-270° C. obtained by catalytically cracking petroleum and subjected to the preliminary treatment in the presence of the acidic catalyst at a temperature of 120°-200° C. and with a liquid phase space velocity of 0.2-2 Hr$^{-1}$ and then to a fractional distillation step.

8. The process as set forth in claim 6, in which the starting mixture material containing methyl naphthalenes is a fraction with b.p. of 220°-250° C. obtained by catalytically cracking petroleum and subjected to the preliminary treatment in the presence of the acidic catalyst at a temperature of 120°-200° C. and with a liquid phase space velocity of 0.2-2 Hr$^{-1}$ and then to a fractional distillation step.

9. The process as set forth in any of claims 1-8, in which the acid catalyst is a solid catalyst or a liquid catalyst used generally for olefin polymerization.

10. The process as set forth in claim 9, in which the liquid catalyst is sulfuric acid or phosphoric acid.

11. The process as set forth in claim 9, in which the solid catalyst is silica, alumina, silica-alumina, chromia, titania, zirconia, chromia-alumina, clay, bauxite, zeolite, activated carbon or activated clay.

12. The process as set forth in claim 11, in which the solid catalyst has a surface area of 100-500 m$^2$/g, an average porous diameter of 30-300 Å, a porous volume of 0.1-1.0 cc/g and a particle dimension of 10-100 mesh.

13. The process as set forth in claim 11, in which activated clay catalyst is of montmorillonite system having 2:1 layer structure.

14. The process as set forth in claim 2, in which the starting mixture material is preliminarily treated in the presence of the acid catalyst at a raised temperature up to 220° C. at the highest and with a liquid phase space velocity of 0.1-6 Hr$^{-1}$.

15. The process as set forth in claim 14, in which the starting mixture material containing dimethyl naphthalenes is a fraction with b.p. of 250°-270° C. obtained by catalytically cracking petroleum and subjected to the preliminary treatment in the presence of the acidic catalyst at a temperature of 120°-200° C. and with a liquid phase space velocity of 0.2-2 Hr$^{-1}$ and then to a fractional distillation step.

16. The process as set forth in claim 3, in which the starting mixture material is preliminarily treated in the presence of the acid catalyst at a raised temperature up to 220° C. at the highest and with liquid phase space velocity of 0.1-6 Hr$^{-1}$.

17. The process as set forth in claim 16, in which the starting mixture material containing methyl naphthalene is a fraction with b.p. of 220°-250° C. obtained by catalytically cracking petroleum and subjected to the preliminary treatment in the presence of the acidic catalyst at a temperature of 120°-200° C. and with a liquid phase space velocity of 0.2-2 Hr$^{-1}$ and then to a fractional distillation step.

* * * * *